United States Patent
Nevins et al.

(10) Patent No.: US 11,045,263 B1
(45) Date of Patent: Jun. 29, 2021

(54) SYSTEM AND METHOD FOR GENERATING A VIRTUAL JIG FOR SURGICAL PROCEDURES

(71) Applicants: Russell Nevins, Las Vegas, NV (US); David Jon Backstein, Toronto (CA); Bradley H. Nathan, Toronto (CA)

(72) Inventors: Russell Nevins, Las Vegas, NV (US); David Jon Backstein, Toronto (CA); Bradley H. Nathan, Toronto (CA)

(73) Assignees: Russell Nevins, Las Vegas, NV (US); David Jon Backstein; Bradley H. Nathan

( * ) Notice: Subject to any disclaimer, the term of this patent is extended or adjusted under 35 U.S.C. 154(b) by 0 days.

(21) Appl. No.: 16/788,198

(22) Filed: Feb. 11, 2020

Related U.S. Application Data

(60) Provisional application No. 62/948,760, filed on Dec. 16, 2019.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *G02B 27/017* (2013.01);
(Continued)

(58) Field of Classification Search
CPC .............. A61B 34/10; A61B 2034/102; A61B 2034/104; A61B 2034/107;
(Continued)

(56) References Cited

U.S. PATENT DOCUMENTS

| 7,812,815 B2 | 10/2010 | Banerjee |
| 8,123,754 B2 | 2/2012 | Siebel |

(Continued)

FOREIGN PATENT DOCUMENTS

| WO | WO-2018132804 A1 * | 7/2018 | ......... A61B 17/1703 |

OTHER PUBLICATIONS

Microsoft HoloLens & Mixed /Reality Healthcare Industry Deck, unknown author, at least as early as Oct. 14, 2019.

(Continued)

*Primary Examiner* — Larry E Waggle, Jr.
(74) *Attorney, Agent, or Firm* — Morriss O'Bryant Compagni Cannon, PLLC

(57) ABSTRACT

A system and method for generating a surgical instrument in a surgical procedure is disclosed. The method may include, attaching a grid to a portion of a patient's body and using a mixed or augmented reality system to produce a virtual instrument, or holographic representation of a physical instrument. The user can the manipulate the virtual instrument to a desired position on the patient's body, and using coordinates on a grid, identifies a desired location of the virtual instrument with respect to the patient's body. The user may then drill holes that correspond with the positioning of the virtual instrument and identified by coordinates on the grid, and the attach the physical instrument to the desired location using holes drilled at the identified coordinates.

22 Claims, 11 Drawing Sheets

(51) Int. Cl.
  *G06T 19/00* (2011.01)
  *G06T 19/20* (2011.01)
  *G02B 27/01* (2006.01)

(52) U.S. Cl.
  CPC .......... *G06T 19/003* (2013.01); *G06T 19/006* (2013.01); *G06T 19/20* (2013.01); *A61B 2034/102* (2016.02); *A61B 2034/104* (2016.02); *A61B 2034/105* (2016.02); *A61B 2034/107* (2016.02); *A61B 2034/108* (2016.02); *A61B 2034/2068* (2016.02); *G02B 2027/0174* (2013.01); *G06T 2210/41* (2013.01)

(58) Field of Classification Search
  CPC .............. A61B 2034/108; A61B 34/20; A61B 2034/2068; G02B 27/017; G02B 2027/0174; G06T 2210/41; G06T 19/003; G06T 19/006; G06T 19/20
  See application file for complete search history.

(56) References Cited

U.S. PATENT DOCUMENTS

| | | | |
|---|---|---|---|
| 8,876,830 | B2 | 11/2014 | Hodorek |
| 8,954,181 | B2 | 2/2015 | MacLeod |
| 8,956,165 | B2 | 2/2015 | Kurenov |
| 9,563,266 | B2 | 2/2017 | Banerjee |
| 9,730,713 | B2 | 8/2017 | Park |
| 9,861,446 | B2 | 1/2018 | Lang |
| 9,980,780 | B2 | 5/2018 | Lang |
| 10,108,266 | B2 | 10/2018 | Banerjee |
| 10,159,530 | B2 | 12/2018 | Lang |
| 10,194,990 | B2 | 2/2019 | Amanatullah |
| 10,220,181 | B2 | 3/2019 | Giap |
| 10,241,569 | B2 | 3/2019 | Lanman |
| 10,278,777 | B1 | 5/2019 | Lang |
| 10,285,765 | B2 | 5/2019 | Sachs |
| 10,286,179 | B2 | 5/2019 | Giap |
| 10,292,768 | B2 | 5/2019 | Lang |
| 10,368,947 | B2 | 8/2019 | Lang |
| 10,401,954 | B2 | 9/2019 | Koker |
| 10,405,873 | B2 | 9/2019 | Amiot |
| 10,405,927 | B1 | 9/2019 | Lang |
| 10,437,335 | B2 | 10/2019 | Daniels |
| 10,437,339 | B2 | 10/2019 | Banerjee |
| 2008/0183179 | A1 | 7/2008 | Siebel |
| 2009/0163923 | A1 | 6/2009 | Flett |
| 2016/0191887 | A1 | 6/2016 | Casas |
| 2017/0245781 | A1 | 8/2017 | Kay |
| 2018/0090029 | A1 | 3/2018 | Fisher |
| 2018/0098813 | A1 | 4/2018 | Nesichi |
| 2018/0116728 | A1 | 5/2018 | Lang |
| 2018/0348876 | A1 | 12/2018 | Banerjee |
| 2019/0076198 | A1* | 3/2019 | Berend .............. A61B 17/1764 |
| 2019/0110842 | A1 | 4/2019 | Lang |
| 2019/0216562 | A1 | 7/2019 | Sachs |

OTHER PUBLICATIONS

Kaluschke et al., HIPS—A Virtual Reality Hip Prosthesis Implantation Simulator, retrieved at https://www.reasearchgate.net/publication/327329265, upload date Sep. 3, 2018 DOI: 10.1109/VR.2018.8446370.

Vaughan et al., Does Virtual-Reality Training on Orthopaedic Simulators Improve Performance in the Operating Room? Science and Information Conference 2015, Jul. 28-30, 2015, London, UK; retrieved at https://www.researchgate.net/publication/284415791; DOI: 10.1109/SAI.2015.7237125.

Patently Apple—Apple Reveals a Mixed Reality Headset that Uses a Direct Retinal Projector System With Holographic Lenses, retrieved at https://www.patentlyapple.com/patently-apple/2019/09/apple-reveals-a-mixed-reality-headset-that-uses-a-direct-retinal-projector-system-with-hologra . . . ; posted date Sep. 19, 2019.

Virtual Reality System Helps Surgeons, Reassures Patients, retrieved at https//medicalgiving.stanford.edu/news/virtual-reality-system-helps-surgeons-reassures-patients.html, retrieved date Oct. 24, 2019.

Immersive Touch Launches the First Virtual Reality Integrated Suite for Surgical Planning, retrieved at https://spinalnewsinternational.com/immersivetouch-virtual-reality-suite, dated Oct. 5, 2018.

Daley, Sam, The Cutting Edge: 10 Companies Bringing Virtual Reality & AR to the OR, retrieved at https://builtin.com/healthcare-technology/augmented-virtual-reality-surgery, dated Jul. 5, 2019.

Barad, Justin, Virtual and Augmented Reality Can Save Lives by Improving Surgeons' Training, retrieved at https://www.statnews.com/2019/08/16/virtual-reality-improve-surgeon-training, dated Aug. 16, 2019.

Levin et al., The Future of Virtual Reality in Ophthalmology Is Already Here, retrieved at https://www.aao.org/young-ophthalmologists/yo-info/article/future-of-virtual-reality-in-ophthalmology, dated Aug. 16, 2019.

Vaughan et al., A Review of Virtual Reality Based Training Simulators for Orthopaedic Surgery, retrieved at https://www.researchgate.net/publication/283727217, posted date Feb. 22, 2019, DOI: 10.1016/j.medengphy.2015.11.021.

LexInnova Patent Landscape Analysis, Virtual Reality, unknown author, copyright date of 2015.

Virtual & Augmented Reality Are You Sure it Isn't Real? Kathleen Boyle, CFA, Managing Editor, Citi GPS dated Oct. 2016.

\* cited by examiner

SYSTEM AND METHOD FOR GENERATING A VIRTUAL JIG FOR SURGICAL PROCEDURES

CROSS-REFERENCE TO RELATED APPLICATIONS

This application claims the benefit of U.S. Provisional Application No. 62/948,760, filed Dec. 16, 2019, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

STATEMENT REGARDING FEDERALLY SPONSORED RESEARCH OR DEVELOPMENT

Not Applicable.

BACKGROUND

1. The Field of the Present Disclosure

The present disclosure relates generally to surgical systems and methods of facilitating the efficiency and accuracy of implanting knee joint prostheses using virtual jigs.

2. Description of Related Art

A conventional knee joint prosthesis typically includes a femoral implant and a tibial implant. The femoral implant and tibial implant are designed to be surgically implanted into the distal end of the femur and the proximal end of the tibia, respectively. The femoral implant is further designed to cooperate with the tibial implant in simulating the articulating motion of an anatomical knee joint.

These femoral and tibial implants, in combination with ligaments and muscles, attempt to duplicate natural knee motion as well as absorb and control forces generated during the range of flexion. In some instances however, it may be necessary to replace or modify an existing femoral and/or tibial implant. Such replacements are generally referred to as revision implants.

To prepare a femur and tibia for such a knee replacement and form an engagement with femoral and tibial implants, the femur and tibia bones must be cut in very specific and precise ways and at very specific and precise angles and locations, so that the prepared bone will properly engage with and be secured to the corresponding implants. In order to make these cuts properly, a surgeon traditionally uses a jig, or surgical cutting guide as known to those skilled in the field, which can be removably attached or secured to the bone, such that slots, or guides, in the jig facilitate the precise cuts necessary to secure the corresponding implants.

The phrase "jig" as used herein, shall thus refer broadly to a surgical cutting guide, that may be secured adjacent to a bone or other tissue to be cut by a surgeon an identify a relative location, angle and or cutting plane that a surgeon should cut on the adjacent bone or tissue, as known in the art. A jig may include predetermined slots and/or cutting surfaces to identify where a surgeon should cut the adjacent bone or tissue, wherein such cuts may correspond to a shape of a surgical implant that may be attached to the cut bone or tissue.

Conventional jigs are typically made of a metal alloy and, due to the precise tolerances at which these jigs must be machined, are quite expensive, ranging as high as $40,000-$50,000 in some cases. These metal jigs must also be stored and reused, which adds additional cost and space resources. Additionally, jigs of various sizes must be kept on had to accommodate patients of different sizes and needs.

Therefore, there is a need for a system that can utilize a less expensive jig, such as a plastic jig, that could be made easily and on demand, while maintaining the required tolerances and enable the same accuracy in use in a surgical procedure.

In other conventional embodiments, holographic jigs, also referred to a virtual jigs, have been used to enable a surgeon to visualize the positioning and proper sizing of a jig to a bone. However, in use, when the surgeon attempts to superimpose a physical jig over the virtual jig to attach it to a bone to make the required bone cuts, the physical jig will impair the view of the virtual or holographic jig, making it difficult to utilize the holographic jig to accurately place the physical jig.

Accordingly, there is a need for a system and method of utilizing a virtual or holographic jig or surgical instrument that could facilitate increased accuracy and precision of required or desired bone cuts.

The phrase "virtual jig" or "holographic jig" as used herein, shall thus refer broadly to any visual rendering or projection representing an actual physical jig, having all, or mostly all, of the same visual characteristics of the physical jig, including size and shape, as known in the art.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims. Any discussion of documents, acts, materials, devices, articles or the like which has been included in the present specification is not to be taken as an admission that any or all of these matters form part of the prior art base, or were common general knowledge in the field relevant to the present disclosure as it existed before the priority date of each claim of this application.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
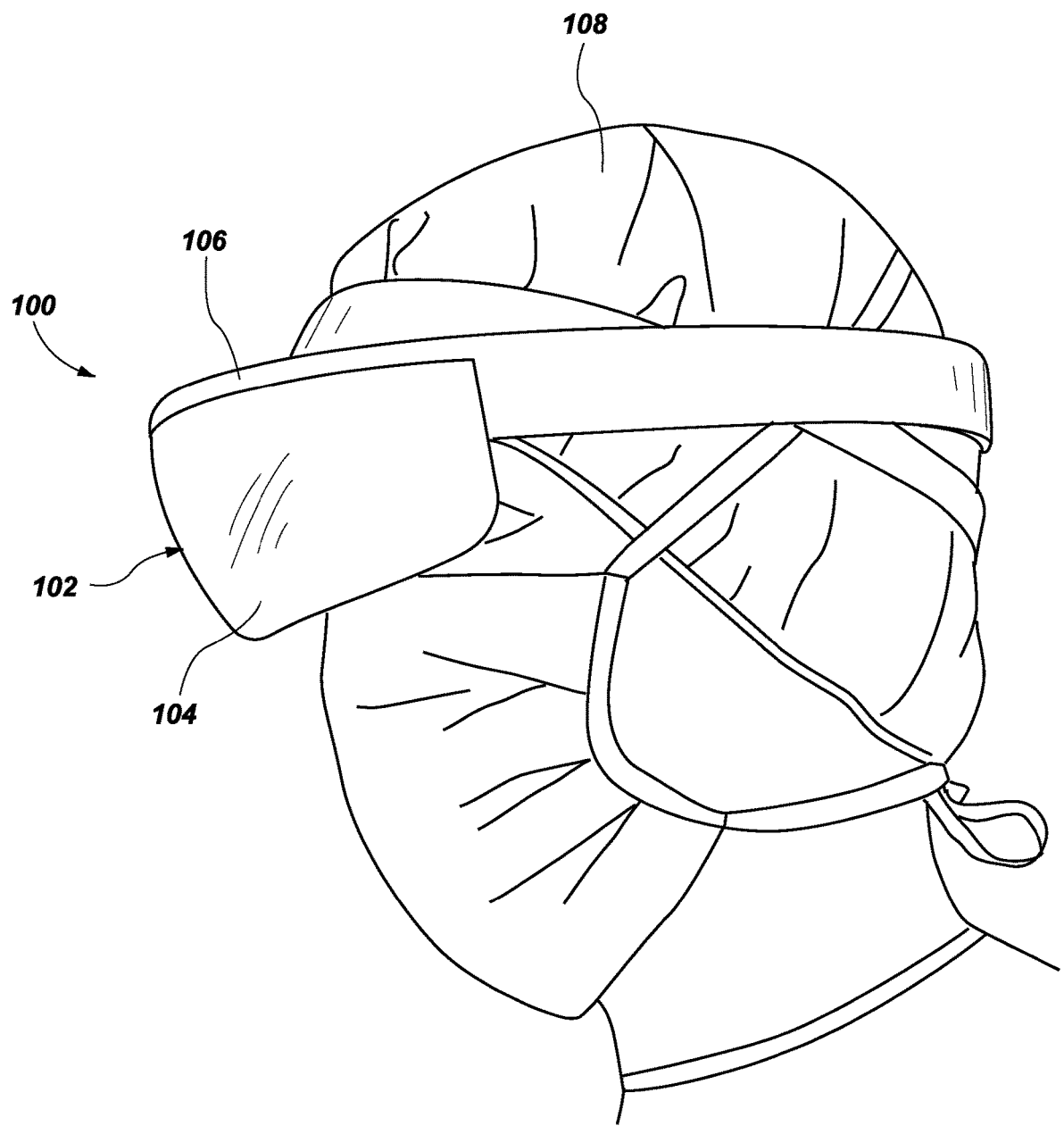
FIG. 1 is a perspective view of a user wearing a mixed or augmented reality headset of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the terms "virtual," and "hologram" are used interchangeably, and grammatical equivalents thereof are inclusive or open-ended terms that do not exclude additional, unrecited elements or method steps. These terms are used to describe visual representations of an actual physical device or element, having all, or mostly all, of the same visual characteristics of the physical device, including size and shape.

Applicant has discovered a novel system and method for generating and using a virtual jig, or virtual instrument, in a surgical procedure, for example, in a knee or tibial implant procedure, or other desired surgical procedure.

The phrase "virtual system" as used herein, shall refer broadly to any system capable of generating or creating a simulated or virtual rendering or projection of physical or structural features identical or substantially identical to an actual physical device, instrument or other physical structure, as known in the art. A virtual system may also include a device, mechanism, or instrument capable of projecting or displaying the desired a simulated or virtual rendering or projection of physical or structural features identical or substantially identical to an actual physical device. A virtual system may also enable a user to manipulate, move and/or modify the simulated or virtual rendering or projection.

The phrase "mixed or augmented reality system" as used herein, shall refer broadly to any system capable of generating or creating a simulated or virtual rendering or projection of physical or structural features identical or substantially identical to an actual physical device, instrument or other physical structure, as known in the art. A mixed or augmented reality system may also include a device, mechanism, or instrument capable of projecting or displaying the desired a simulated or virtual rendering or projection of physical or structural features identical or substantially identical to an actual physical device overlaid or concurrently with actual physical structures, mechanism or devices in reality, thus incorporating the virtual rendering or projection in real world settings with actual physical element. A mixed or augmented reality system may also enable a user to manipulate, move and/or modify the simulated or virtual rendering or projection.

The phrase "mixed or augmented reality instrument" as used herein, shall refer broadly to any device, mechanism or instrument used in a mixed or augmented reality system, including a device capable of generating or creating a simulated or virtual rendering or projection of physical or structural features identical or substantially identical to an actual physical device, instrument or other physical structure, as known in the art. A mixed or augmented reality instrument may also be capable of projecting or displaying the desired a simulated or virtual rendering or projection of physical or structural features identical or substantially identical to an actual physical device overlaid or concurrently with actual physical structures, mechanism or devices in reality, thus incorporating the virtual rendering or projection in real world settings with actual physical element. A mixed or augmented reality instrument may also enable a user to manipulate, move and/or modify the simulated or virtual rendering or projection.

The phrase "holographic representation" as used herein, shall refer broadly to a visual rendering or projection representing an actual physical device or element, having all, or mostly all, of the same visual characteristics of the corresponding physical device or element, including size and shape, as known in the art.

Referring to FIG. 1, in a disclosed embodiment a mixed or augmented system 100, which can be used to produce, or display, a desired mixed or augmented reality instrument, such as a virtual jig or cutting guide in a display to a surgeon or user, or stated another way, that is visible and manipulatable by a surgeon or user. The mixed or augmented reality system 100 may also enable a user to activate or deactivate, in full or in part, the virtual instrument or instruments, making a virtual instrument appear or disappear, as desired in a mixed reality assisted surgery, for example. The mixed or augmented reality system 100 may include a mixed or augmented reality headset 102 which may include a transparent or mostly transparent viewer 104 which can be suspended or positioned in front of a user's eyes. The headset 102 may include headband 106 attached to the viewer 104, which may be used to secure the headset 102 to a user's head 108, thereby securing the viewer 104 in place in front of the user's eyes. The transparent viewer 104 may be configured to project, or otherwise make viewable, on an interior surface of the viewer 104, a holographic image or images, such as a virtual jig or cutting guide, which may be positionally manipulated by the user, surgeon, third party or remote system, such as a remote computer system. The headset 102 may be configured to view holographic images or, alternatively, the holographic images may be turned off and the user wearing the headset 102 may be able to view the surrounding environment through the transparent viewer 104, unobstructed. As such, a user, such as a surgeon for example, can wear the mixed or augmented reality headset 102 and then can choose to activate a holographic image to aide in facilitating a surgical procedure and then shut off the holographic image in order to perform the surgical procedure un-obscured, visually.

One embodiment of the disclosed headset 102 may be a product created and manufactured by Microsoft, known as the HoloLens® mixed or augmented reality system, or any suitable mixed or augmented reality system for generating virtual images viewable by a user or surgeon. Headset 102 may be a conventional "off the shelf" product with a built-in platform that enables all of the features described herein with respect to the headset 102. Furthermore, the headset 102, such as a Microsoft HoloLens product, can be loaded or preloaded with all desired or required virtual instruments, including virtual jigs or surgical cutting guides, virtual drill bits and any other desired virtual instruments or holograms. The Microsoft HoloLens product and its capabilities and features, or any suitable mixed or augmented reality system such as is described herein with respect to the headset 102, are known to those skilled in the art.

Figure 2:
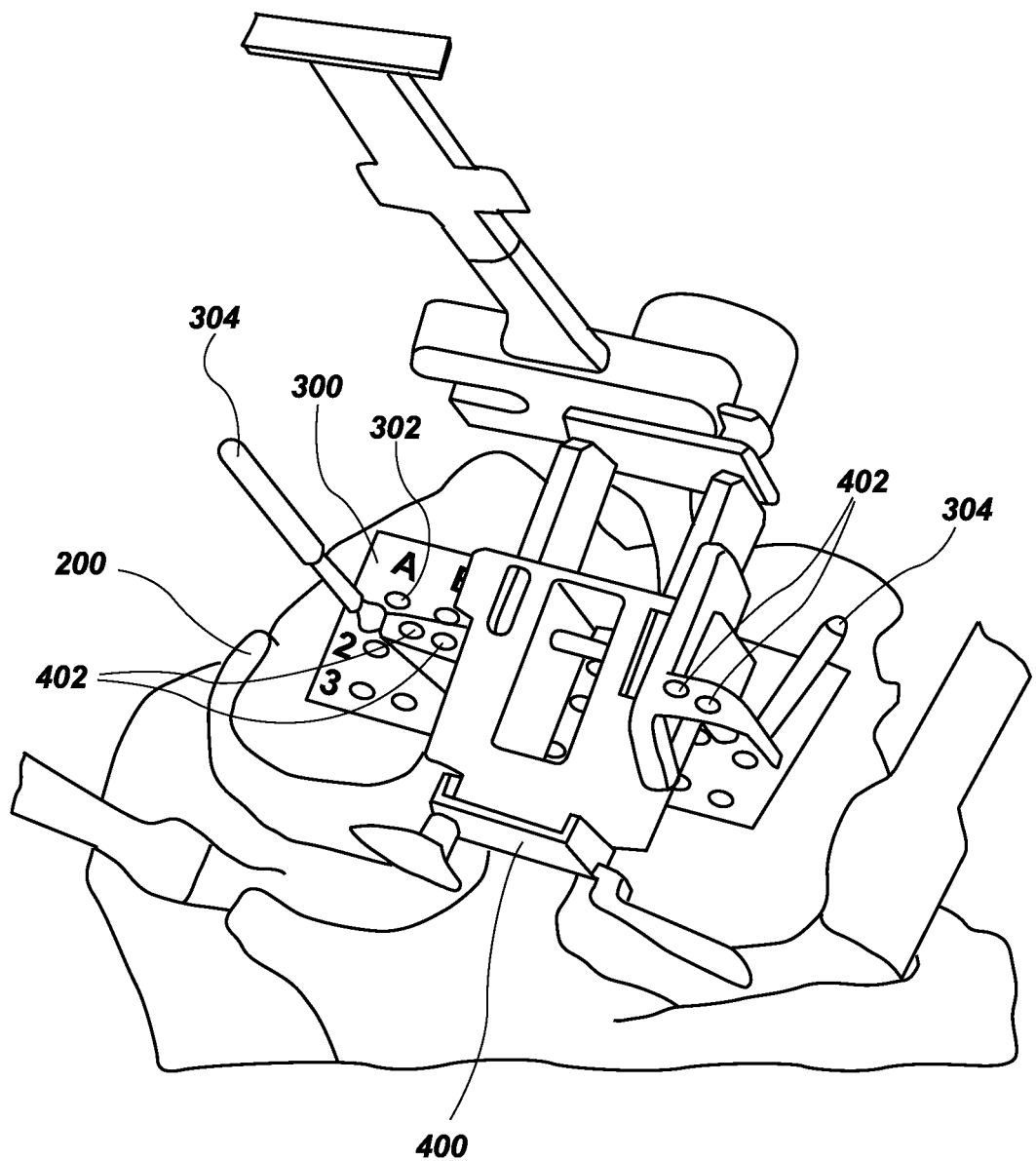
FIG. 2 is a perspective view of a virtual jig and grid positioned on a bone according to the present disclosure.
Figure 3:
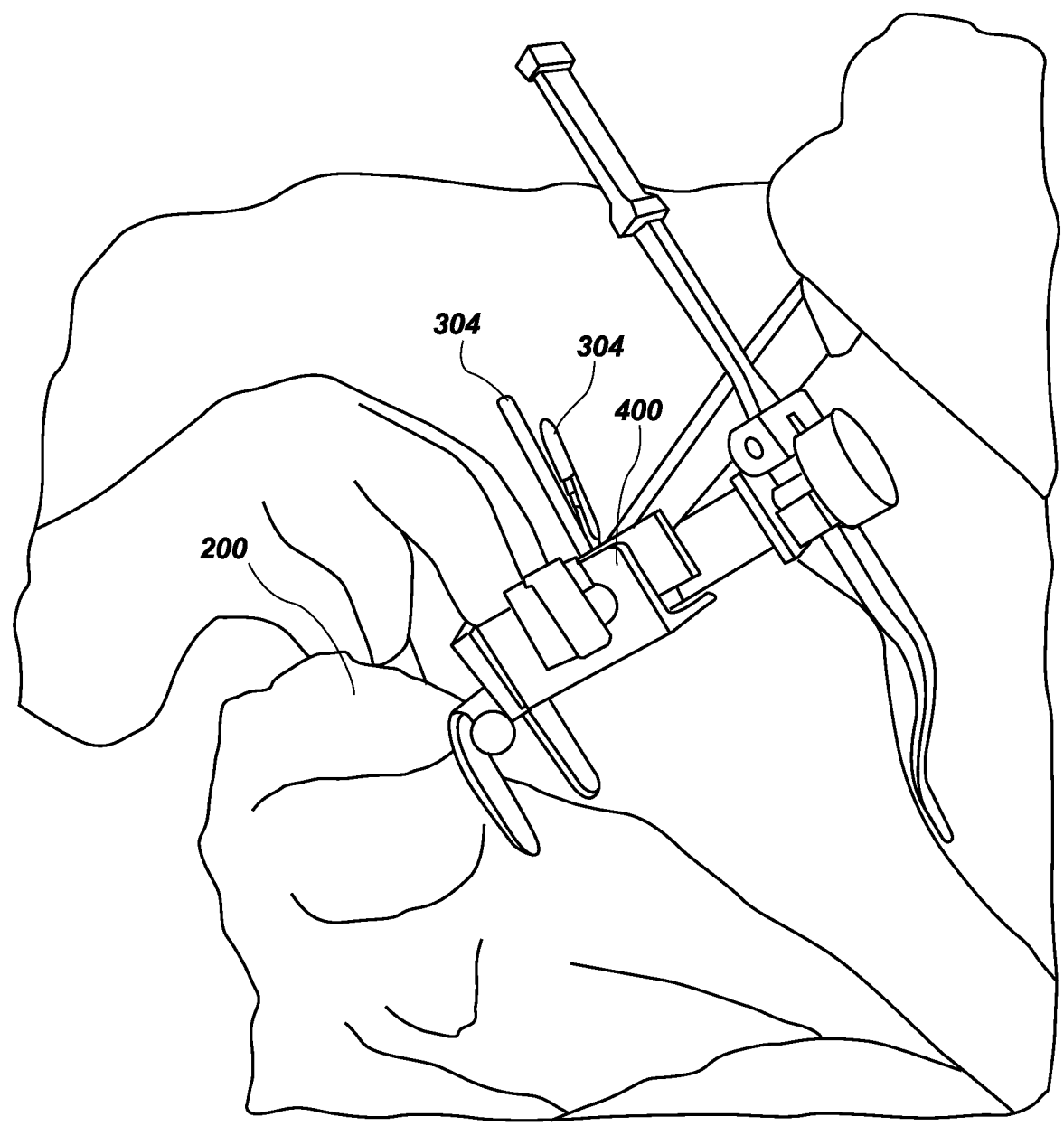
FIG. 3 is a side view of the virtual jig positioned on a bone according to the embodiment of FIG. 2.
Figure 4:
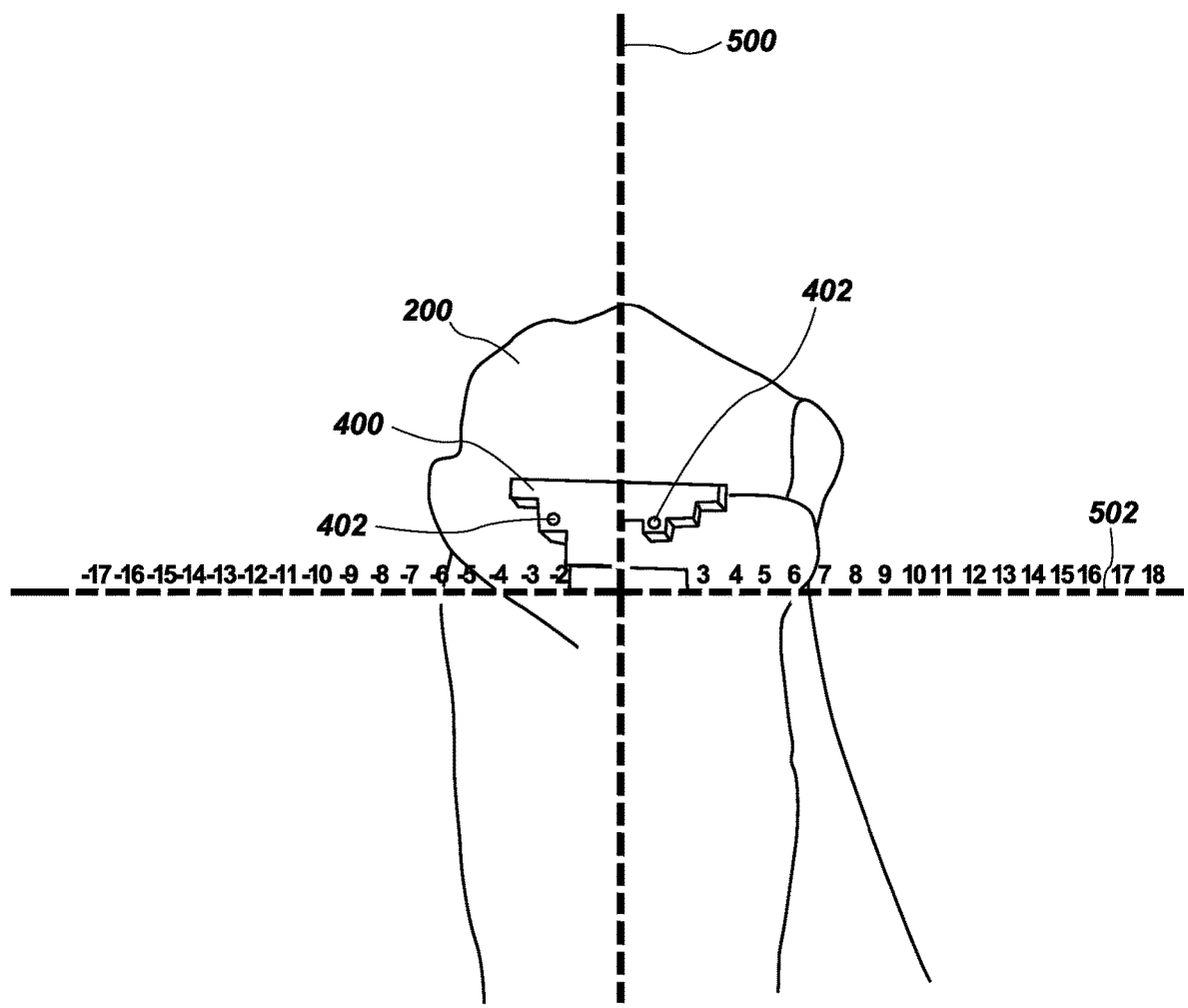
FIG. 4 is a front view of the virtual jig positioned on a bone with corresponding virtual axes of the embodiment of FIG. 2.

Referring to FIGS. 2, 3 and 4, a surgeon may use the disclosed method and an embodiment of the disclosed system, to first expose a desired bone 200 or at least a portion of a desired bone 200 to be surgically repaired or to receive a surgical implant. The surgeon may then prepare a surface of the bone, such as cutting a substantially planar surface of the bone, to receive a surgical jig.

A surgical jig is conventionally, and may be, a surgical tool that may be used to help a surgeon make predetermined and accurate cuts of a desired bone to facilitate attachment of a surgical implant. A jig may have one or a series of slots located at specific predetermined locations and at specific predetermined angles, with respect to a body of the jig, such that when the jig is attached to a bone surface, the surgeon can make precise and accurate cuts, using the jig as a guide, without the need of additional measurements. Once the desired cuts of the bone have been made using the jig as a guide, the jig may be removed from the bone and the surgical implant may be properly secured to the bone which has now been accurately cut to receive the implant.

Once the bone surface 200 is exposed, cut, and/or prepared to receive a jig, the surgeon may attach a grid 300 to the exposed surface of the bone 200.

The term "grid" as used herein, shall refer broadly to a platform that may be planar, substantially planar or contoured, and may include a coordinate pattern that may be represented by a physical, visual and/or virtual medium and may include multiple predetermined columns and rows of indicator points, at any desired level of tolerance or spacing between said points, as known in the art, or may include a pattern of indicator points that is not a coordinate pattern or which does not constitute rows and columns, including randomized patterns. The general shape of the grid may be any desired shape or size, such as, for example, square, rectangular, circular, triangular, or any other desired shape or configuration. The grid may also be made of any desired material, for example, plastic, paper, wax, polyamide, metal, or any other desired material. The columns and rows of indicator points may be linear, substantially linear, curved, or the indicator points may be positioned in any desired pattern or randomly positioned without a distinct pattern.

The phrase "indicator points" as used herein, shall refer broadly to any visual or physical marker that may be used to identify a specific location on a surface or platform, such as a grid, for example. The indicator points may be of any predetermined size or shape. The indicator points may be holes that extend through the grid or may be markers visible on a top surface of a grid or other platform or surface. Indicator points my include or be represented by numbers, letters, colors, patterns, pictures or drawings, or any other desired visual representation. Indicator points may also include physical features such as contours, hills, valleys, grooves, divots, braille, ribs or any other desired physical feature that may be used to identify a specific location on a surface, platform or grid, for example.

In further reference to FIGS. 2, 3 and 4 and the foregoing paragraph, the grid 300 may therefore be attached to an exposed bone that has not been cut, or has been cut already, depending on the needs and desired of the surgeon performing a procedure. The grid 300 may include multiple predetermined columns and rows of indicator points 302, at any desired level of tolerance or spacing between indicator points. These indicator points 302 may for example be equally spaced from one another at predetermined distances. The indicator points may also be of a predetermined size, for example, to match a circular diameter of a desired drill bit, attachment pin, or other simply some other desired size or shape. The rows and columns of indicator points 302, may essentially form a coordinate pattern on the grid 300, which can enable a surgeon to locate a virtual jig 400 at a desired location with respect to the bone 200. The grid 300 may also be made of metal, plastic, polyamide or any other desired material.

The phrase "pin" as used herein, shall refer broadly to a fastener, stake, staple, rod or other device or mechanism that may pass through at least two objects, releasably securing them together, as known in the art.

The indicator points 302 may be circular holes, square holes, slots, or formed in any other desired geometric shape. The indicator points 302 may be configured of any desired size, for example, indicator points 302 may be configured to receive a 3.2 mm drill bit, or any other desired drill bit size. In another example, the indicator points 302 may be holes of 3.5 mm diameter, or any other desired diameter or size.

The grid 300 may be removably fixed or secured to the bone 200 via pins 304 which may be removably inserted through the grid 300 and into the bone 200. Alternatively the grid 300 may be removably secured or fixed to the bone via some other desired mechanism, such as staples, temporary adhesive, or some other desired attachment mechanism, for example.

Once the grid 300 is secured to the bone 200, the surgeon may activate the mixed or augmented reality headset 102, to activate a holographic image, such as the holographic or virtual jig 400. The virtual jig 400 can match the same physical dimensions of a desired physical jig required to make the required bone cuts for engagement with a desired bone implant. The headset 102 may be configured with compatible software that can enable the surgeon to pick a desired virtual jig type and size, to match the needs of a patient's bone 200, and then enable the surgeon to manipulate the positioning of the virtual jig 400 with respect to the bone 200.

Accordingly, the surgeon may be able to superimpose the virtual jig over the bone 200 and grid 300, in a display viewable by the surgeon or user, viewable with the headset 102. The surgeon may also be able to manipulate the virtual jig 400 in that display to achieve a proper desired position with respect to the bone 200. Manipulation of the virtual jig 400 may be accomplished via hand movements of the surgeon, voice activation, or specified key strokes on a linked computer or other compatible electronic device that may be paired and/or electronically linked with the headset 102. The linking between the headset 102 and a remote computer system may be accomplished via WiFi, bluetooth, hardwired or any other desired electronic communication platform or format.

Figure 5:
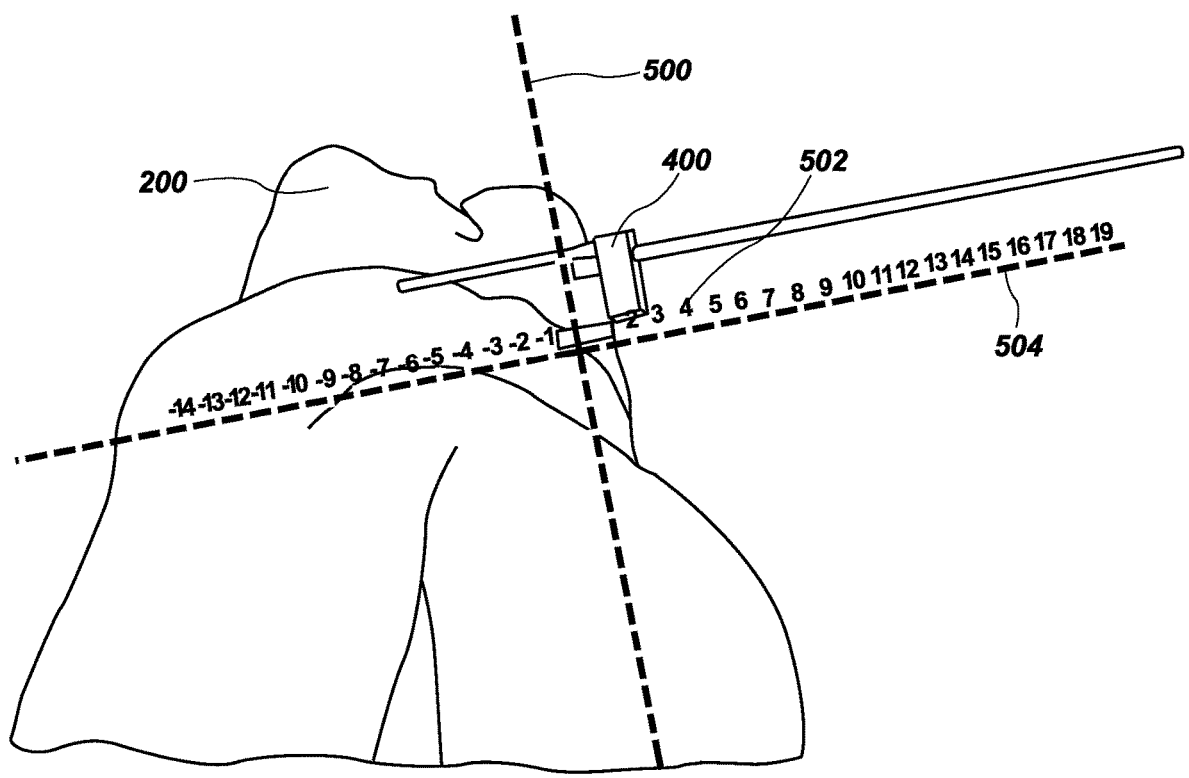
FIG. 5 is a side view of the virtual jig positioned on a bone with corresponding virtual axes of the embodiment of FIG. 2.
Figure 6:
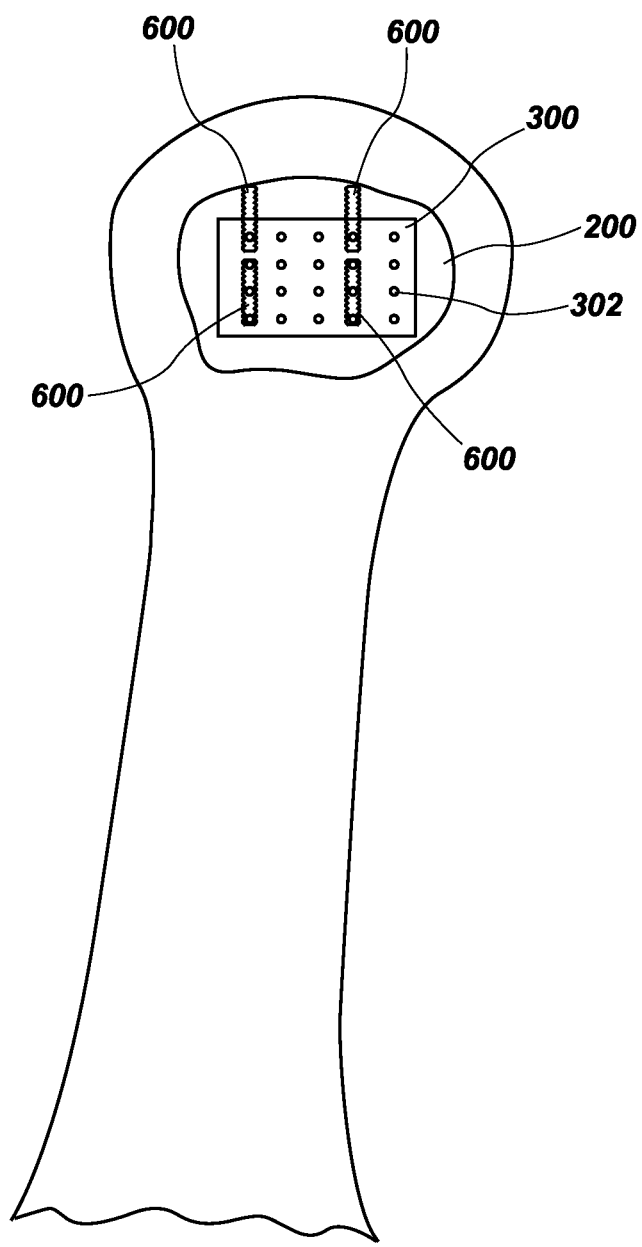
FIG. 6 is a front view of virtual drill bits superimposed on a grid positioned on a bone.

As shown in FIGS. 4 and 5, the compatible software of the mixed or augmented reality headset 102 may also include virtual axes 500, 502 and 504 (such as x, y and z axes) which may further aid the surgeon in properly and accurately manipulating and positioning the virtual jig 400. The software may further aid the surgeon by changing the color of the corresponding axis 500, 502, or 504 when the virtual jig is proper aligned with respect to the bone, for example. Or the software may provide another desired visual indicator when the jig is properly and accurately aligned with respect to the corresponding axes 500, 502, and/or 504.

Additionally, the compatible software of the mixed or augmented reality headset 102 may be capable of identifying physical attributes and characteristics of the bone 200 and automatically orient the virtual jig 400 in a proper desired position with respect to the bone 200. Further, the mixed or augmented reality headset 102 may include virtual representations of potential cutting planes to simulate where and how a cut would be made, given a particular positioning and orientation of the virtual jig 400 or other virtual instrument.

Once the virtual jig 400 is positioned at the proper location with respect to the bone 200 the virtual jig 400 can be held or anchored in place with respect to the bone. The virtual jig 400 at this proper or desired location, may be superimposed over the grid 300. The virtual jig 400 may also include at lease one, or multiple, drill holes 402, which correspond with drill holes in the physical corresponding jig.

When the virtual jig 400 is positioned at the proper desired location, the drill holes 402 may also be superimposed over the grid 300. The surgeon can then locate the coordinates or indicator points 302 that correspond to the drill holes 402 and record the corresponding locations on the grid 300.

Once the virtual jig 400 position and drill holes 402 positions are identified and recorded, the surgeon can turn off, hide or otherwise deactivate, in full or at least a portion of, the virtual jig 400 on the viewer 104 of the mixed or augmented reality headset 102. Then, if desired, the surgeon can activate holographic or virtual drill bits 600, which can be formed of any desired size or shape, for example. The virtual drill bits 600 can also be sized and oriented by the mixed or augmented reality headset 102 and compatible software, to aid and facilitate the surgeon drilling actual physical drill bits or pins into the bone 200 at the proper location on the bone 200 to facilitate the earlier recorded placement of the virtual jig 400 drill holes 402.

The compatible software and headset 102 can provide a visual indicator when the drill and drill bit are oriented at the proper angle and location with respect to the bone 200. The compatible software and mixed or augmented reality headset 102 may be preloaded with desired and necessary virtual instruments and/or jigs and corresponding virtual drill bits, or in another example, the corresponding physical drill bits and physical jigs may have self identifying codes or scanable identifiers, such as a QR code (Quick Response) sticker, for example, which can then be used to access the corresponding virtual jig and/or virtual drill bit or pin.

Figure 7:
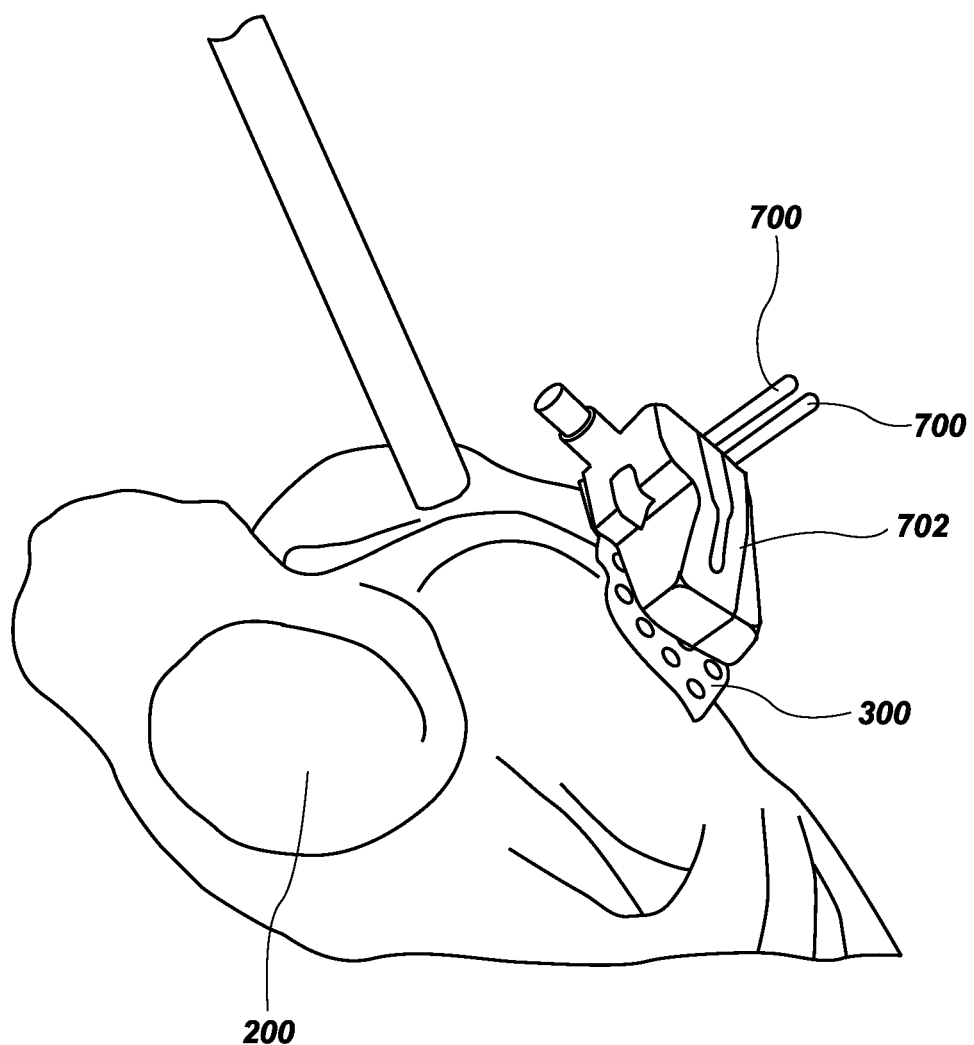
FIG. 7 is a perspective view of a physical jig secured to a bone.

Referring to FIG. 7, once a physical drill bit or pins 700 are drilled into the bone 200 at the proper position and at the proper angle, the corresponding physical jig 702 can be slipped onto the pins 700 which secure the physical jig 702 into the desired and proper location and orientation with respect to the bone 200.

As described above, once the surgeon has identified and recorded the desired and proper orientation of the virtual jig 400 superimposed on the grid 300, the surgeon will need to deactivate or turn off, in full or at least a portion of, the virtual jig 400 and rely on the identified and recorded coordinates to drill the proper corresponding holes. Without deactivating the virtual jig 400 the surgeon will have significant difficulty making accurate drill holes because the actual drill, drill bit or other required instrument would need to be superimposed over the virtual jig 400 which would then impair the surgeon's view of the precise location and orientation of the proper drill holes. The disclosed method of drilling the proper corresponding holes for the actual physical jig 702 avoids this potential inaccuracy, by relying on the coordinates on the grid 300, which are physical representations and therefore will not be blocked or otherwise impaired when the surgeon makes the required drill holes.

Due to the accuracy of the disclosed method and system, the physical jig 702 may be made of plastic, metal, polyamide, or any other desired material. Manufacturing the physical jig 702 out of a plastic or polyamide material, or other relatively inexpensive material, may allow the physical jig 702 to be disposable, while still maintaining the precision and accuracy of traditional metal jigs. The physical jig 702 may also be manufactured using a 3D printer, which can further reduce the cost of manufacturing and storage of jigs, since 3D printed jigs could be made on demand, customized to the size and shape required by individual patients and users. The physical jig 702 may also be manufactured using any other known technique for forming a physical jig.

Additionally, as described above, the compatible and the corresponding locations and orientations of the virtual drill bits 600, may be activated on the virtual headset 102 after at least a portion of the virtual jig 400 has been deactivated. Because the virtual drill bits 600 may have the same geometric and physical attributes as the actual physical drill bits 700, the surgeon may use the virtual drill bits 600 as a drilling guide of the actual physical drill bits without risking inaccuracy due to any potential interference between the virtual drill bits 600 and the physical drill bits 700, during drilling of the actual physical drill bits.

Figure 8:
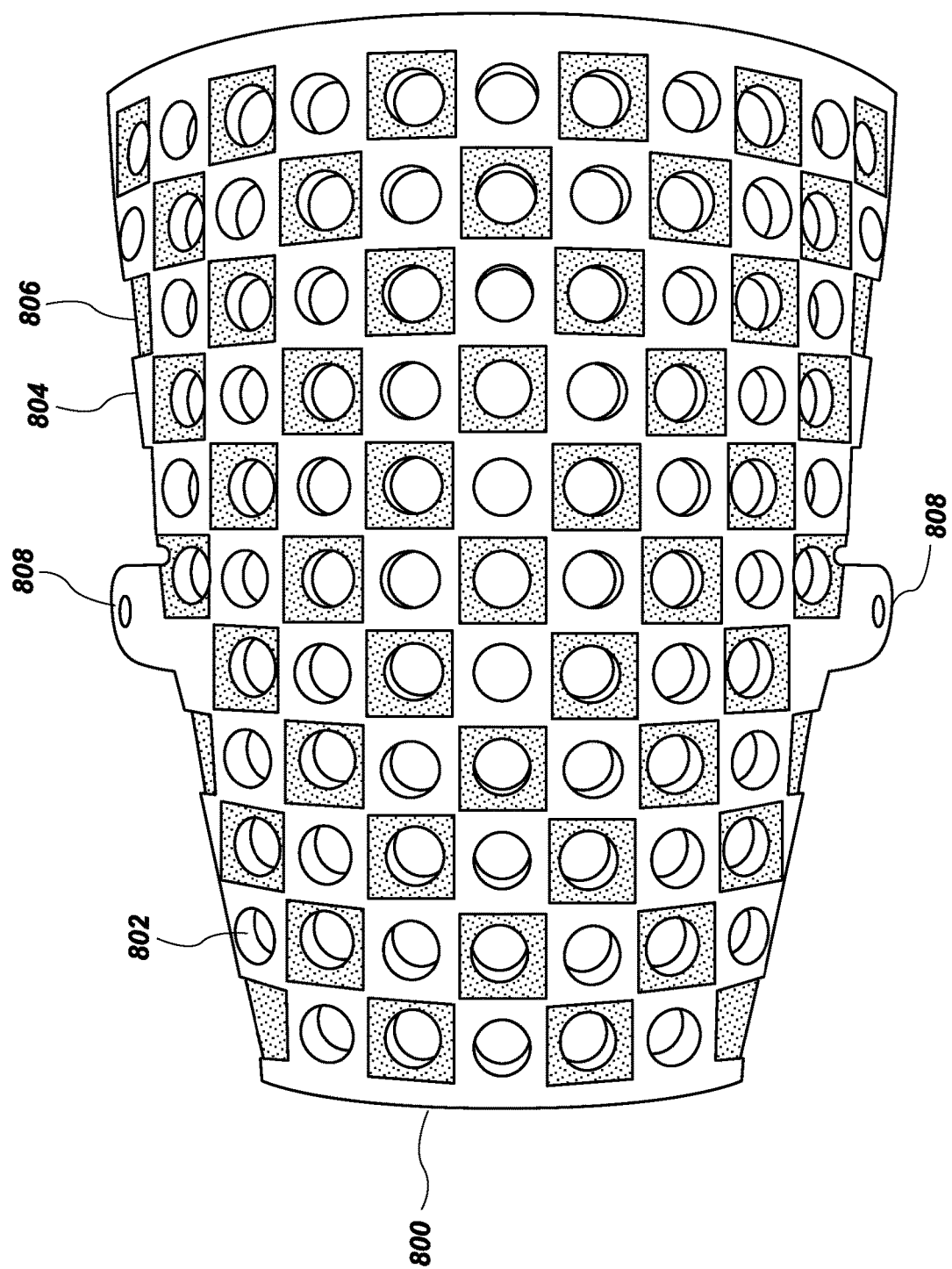
FIG. 8 is a top view of a grid according to an embodiment of the disclosure.

Referring to FIG. 8, once a bone has been prepared to receive a jig, the surgeon may attach a grid 800 to the exposed surface of a bone, as similarly done with respect to grid 300 disclosed above. Therefore, the grid 800 may be attached to an exposed bone that has not been cut, or has been cut already, depending on the needs and desired of the surgeon performing a procedure. The grid 800 may include multiple predetermined columns and rows of indicator points 802, at any desired level of tolerance or spacing between grid holes. These indicator points 802 may for example be equally spaced from one another at predetermined distances. The indicator points 802 may also be of a predetermined size, for example, to match a circular diameter of a desired drill bit, attachment pin, or other simply some other desired size or shape.

The rows and columns of indicator points 802, may essentially form a coordinate pattern on the grid 800, which can enable a surgeon to locate a virtual jig 400 at a desired location with respect to a bone. For example, each indicator point may be centered within a square 804 or 806 which may have structural features that alternate square 804 to square 806, ti enable a surgeon or user to better visualize the coordinate pattern on the grid 800. Additionally, for example, squares 804 may be white in color and squares 806 may be black in color, or squares 804 and 806 can be any other contrasting colors, which can further improve the visual identification of the coordinate pattern. Squares 804 may also have a raised surface with respect to adjacent square 806, which may include a sunken surface or counterbored surface, for example, which also can further improve the visual identification of the coordinate pattern. These structural distinctions between adjacent squares 804 and 806, may also be utilized by the headset 102 during spatial mapping, to facilitate identification and positioning of three dimensional vectors for virtual jigs 400 and/or virtual drill bits.

Each of the squares 804 and 806 may be of any desired size to accommodate the corresponding indicator points 802, for example, each square may have 5.5 mm sides, or any other desired size. The squares 804 and 806, may also be formed in any desired shape, such as rectangular, triangular or any other desired shape. The grid 800 may also be made of metal, plastic, polyamide or any other desired material.

The indicator points 802 may be circular holes, square holes, slots, or formed in any other desired geometric shape. The indicator points 802 may be configured of any desired size, for example, indicator points 302 may be configured to receive a 3.2 mm drill bit, or any other desired drill bit size. In another example, the indicator points 302 may be holes of 3.5 mm diameter, or any other desired diameter or size.

The grid 800 may be removably fixed or secured to a bone via pins (not shown) which may be removably inserted through the grid 800 at predetermined holes 808 and into the adjoining bone. Alternatively the grid 800 may be removably secured or fixed to the bone via some other desired mechanism, such as staples, temporary adhesive, or some other desired attachment mechanism, for example.

Figure 9:
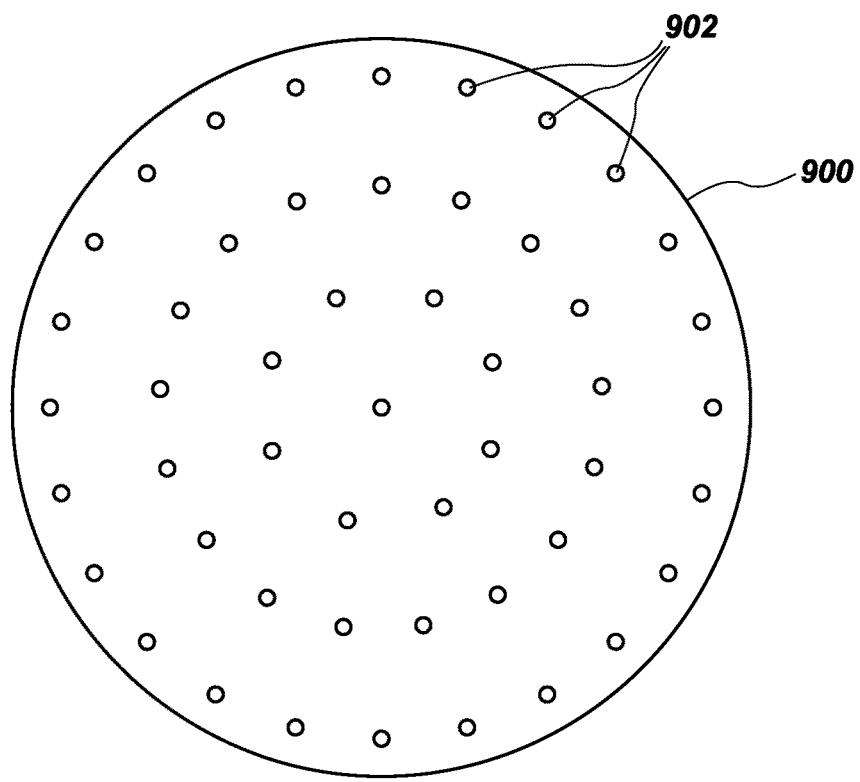
FIG. 9 is a top view of another grid according to an embodiment of the disclosure.

FIG. 9 illustrates another embodiment which includes a grid 900 which may be used in the same way described with respect to grid 800 above. A surgeon may attach grid 900 to an exposed surface of a bone, as similarly done with respect to grids 300 and 800 disclosed above. The grid 900 may be formed in a substantially circular shape, or any other desired shape, and include a series of indicator points 902, at any desired level of tolerance or spacing between adjacent indicator points 902. These indicator points 902 may be position in substantially concentric circular patterns, as shown in FIG. 9, or in any other desired pattern. The indicator points 902 may be holes or visual markers and may be of any predetermined size, for example, to match a circular diameter of a desired drill bit, attachment pin, or other any other desired size or shape.

Figure 10:
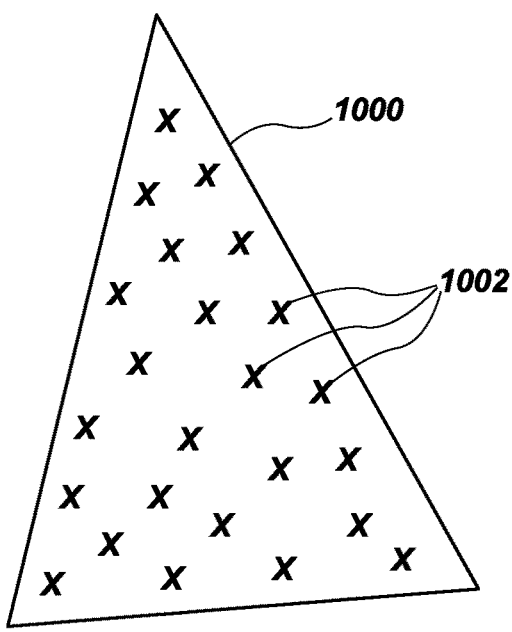
FIG. 10 is a top view of another grid according to an embodiment of the disclosure.

FIG. 10 illustrates another embodiment which includes a grid 1000 which may be used in the same way described with respect to grid 800 above. A surgeon may attach grid 1000 to an exposed surface of a bone, as similarly done with respect to grids 300 and 800 disclosed above. The grid 1000 may be formed in a substantially triangular shape, or any other desired shape, and include a series of indicator points 1002, at any desired level of tolerance or spacing between adjacent indicator points 1002. These indicator points 1002 may be position in substantially in a random pattern, as shown in FIG. 10, or in any other desired pattern. The indicator points 1002 may be "x"s, holes or other desired visual markers and may be of any predetermined size, for example, to match a circular diameter of a desired drill bit, attachment pin, or other any other desired size or shape.

Figure 11:
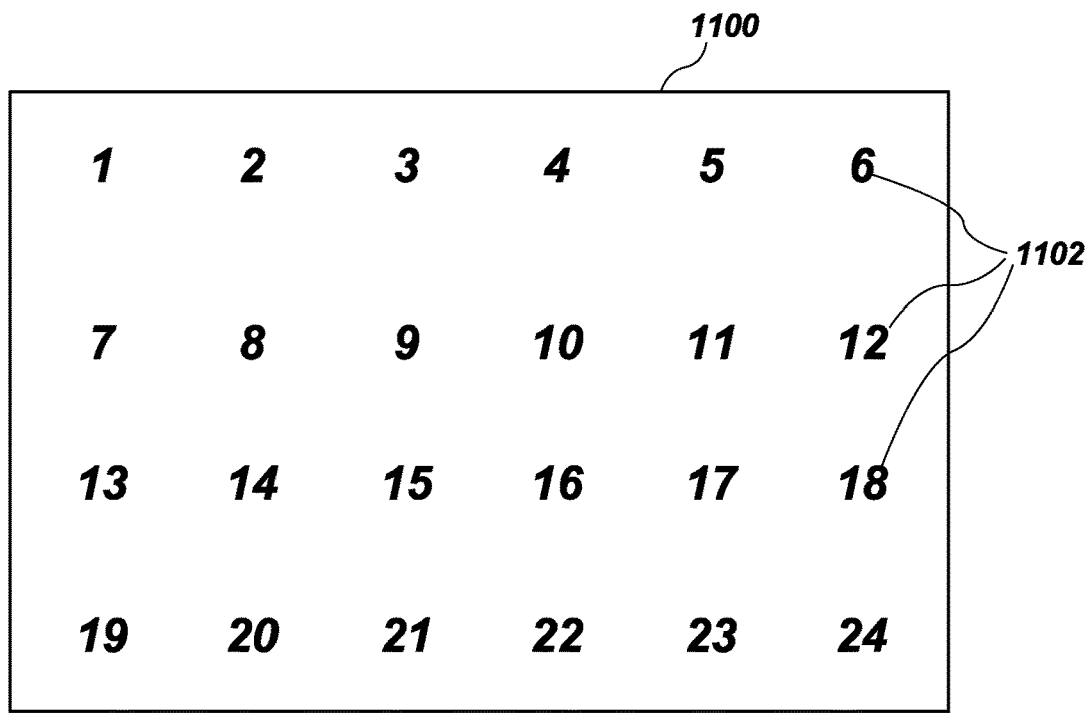
FIG. 11 is a top view of another grid according to an embodiment of the disclosure.

FIG. 11 illustrates another embodiment which includes a grid 1100 which may be used in the same way described with respect to grid 800 above. A surgeon may attach grid 1100 to an exposed surface of a bone, as similarly done with respect to grids 300 and 800 disclosed above. The grid 1100 may be formed in a substantially rectangular shape, or any other desired shape, and include a series of indicator points 1102, at any desired level of tolerance or spacing between adjacent indicator points 1102. These indicator points 1102 may be position in substantially in rows and columns, as shown in FIG. 11, or in any other desired pattern. The indicator points 1102 may be numbers, holes or other desired visual markers and may be of any predetermined size, for example, to match a circular diameter of a desired drill bit, attachment pin, or other any other desired size or shape.

Figure 12:
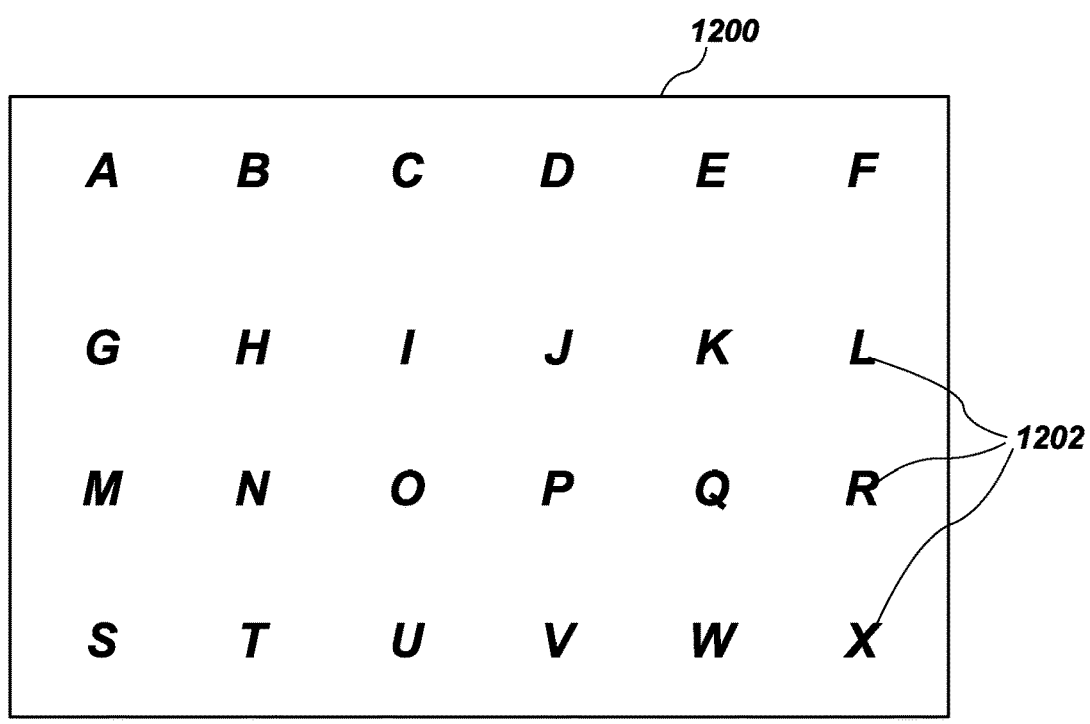
FIG. 12 is a top view of another grid according to an embodiment of the disclosure.

FIG. 12 illustrates another embodiment which includes a grid 1100 which may be used in the same way described with respect to grid 800 above. A surgeon may attach grid 1200 to an exposed surface of a bone, as similarly done with respect to grids 300 and 800 disclosed above. The grid 1200 may be formed in a substantially rectangular shape, or any other desired shape, and include a series of indicator points 1202, at any desired level of tolerance or spacing between adjacent indicator points 1202. These indicator points 1202 may be position in substantially in rows and columns, as shown in FIG. 12, or in any other desired pattern. The indicator points 1202 may be letters, holes or other desired visual markers and may be of any predetermined size, for example, to match a circular diameter of a desired drill bit, attachment pin, or other any other desired size or shape.

Figure 13:
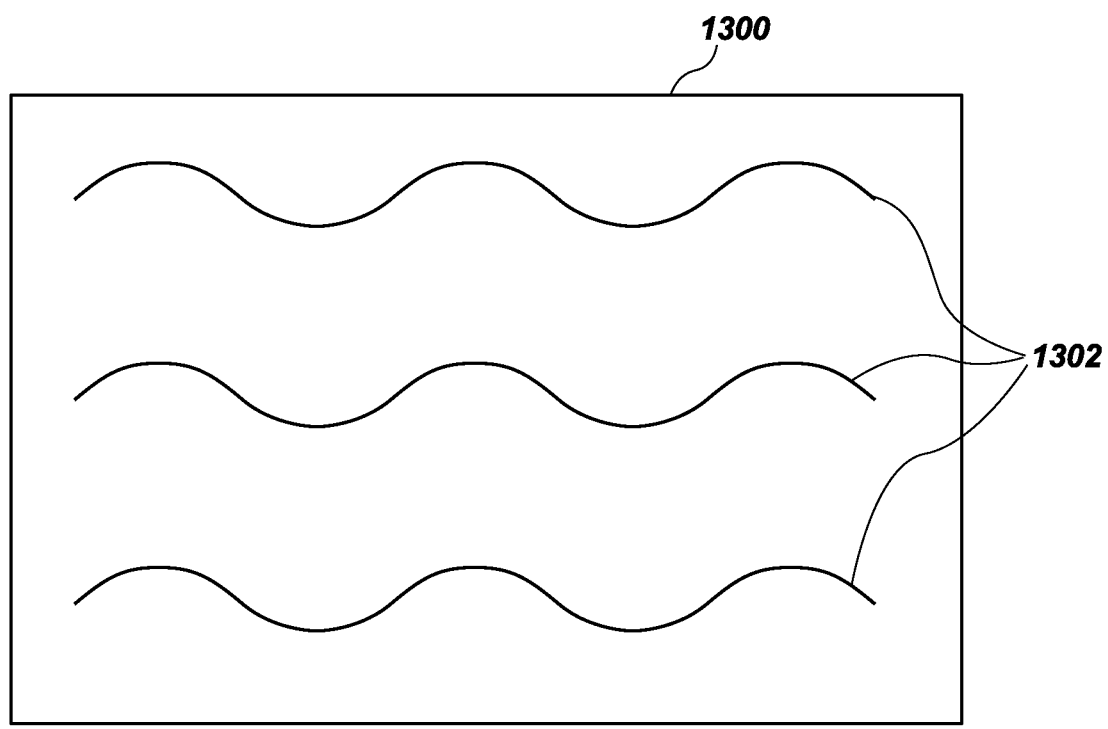
FIG. 13 is a top view of another grid according to an embodiment of the disclosure.

FIG. 13 illustrates another embodiment which includes a grid 1300 which may be used in the same way described with respect to grid 800 above. A surgeon may attach grid 1300 to an exposed surface of a bone, as similarly done with respect to grids 300 and 800 disclosed above. The grid 1300 may be formed in a substantially rectangular shape, or any other desired shape, and include a series of indicator points 1302, at any desired level of tolerance or spacing between adjacent indicator points 1302. These indicator points 1302 may be position in substantially in rows and columns, as shown in FIG. 13, or in any other desired pattern. The indicator points 1302 may be contours, hills and valleys, or other desired visual or physical markers and may be of any predetermined size.

In another embodiment the compatible software and mixed or augmented reality headset 102 may provide the surgeon with holographic or virtual rulers or measurement devices, which can be used and manipulated by the surgeon to measure physical features of the bone, such as medial or later side of the bone, or knee for example, to determine where initial cuts to the bone should be made, such as initial cuts to a femur or tibial in a knee replacement procedure, for example. These virtual measurement devices may also aid a surgeon in confirming proper orientation of the virtual jig 400 with respect the bone.

In other embodiments, the compatible software and mixed or augmented reality headset 102 may enable a surgeon or user to make other surgical procedure on various parts and bone of a body, using similar methodology as provided above with respect to a virtual and actual jig, utilizing a grid similar to the disclosed grid 300, and following the same substantive steps of activating and deactivating the virtual jig (or other desired instrument), and relying on the coordinates of the grid 300.

In still other embodiments, the disclosed system and method of utilizing a virtual instrument superimposed over a physical grid to identify and record the desired orientation and positioning of an actual physical instrument may be useful in other non-analogous fields, such as wall decor and placement, domestic and industrial construction projects, or any other desired filed of use.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A method for generating and using a virtual jig in a surgical procedure, comprising:
    attaching a grid to an exposed portion of a bone;
    using a virtual system to produce a virtual jig, wherein the virtual jig is a holographic representation of a physical jig;
    superimposing the virtual jig over the grid;
    manipulating the virtual jig to a desired position with respect to a bone;
    using the grid to identify the desired position of the virtual jig with respect to the bone;
    drilling holes, slots, or creating a mark for placement of pins, at the identified desired position using the grid, and
    attaching the physical jig to the desired location using holes drilled at the identified desired position.

2. The method of claim 1, further comprising:
    deactivating at least a portion of the virtual jig before drilling the holes or slots or creating the mark.

3. The method of claim 2, further comprising:
    activating at least one virtual drill bit, after deactivating the virtual jig, that corresponds with at least one hole of the virtual jig when the virtual jig is in the desired position.

4. The method of claim 3, further comprising:
    drilling at least one hole corresponding with and aligned with the virtual drill bit and inserting a drill bit or pin into the drilled hole.

5. The method of claim 4, wherein the attaching of the physical jig includes inserting the drill bit or pin, into a corresponding hole in the physical jig.

6. The method of claim 1, wherein the virtual system includes a mixed or augmented reality headset.

7. The method of claim 6, wherein a user wearing the mixed or augmented reality headset manipulates the position of the virtual jig when superimposing the virtual jig over the grid.

8. The method of claim 1, wherein the mixed or augmented reality system includes a mixed or augmented reality headset.

9. The method of claim 1, wherein a user of the mixed or augmented reality system manipulates the position of virtual instrument when superimposing the virtual instrument over the grid.

10. A method for generating and using a virtual instrument in a surgical procedure, comprising:
    exposing a bone;
    attaching a grid to the bone;
    using a mixed or augmented reality system to produce a virtual instrument, wherein the virtual instrument is a virtual representation of a physical instrument;
    superimposing the virtual instrument over the grid;
    using the grid to identify a desired position of the virtual instrument with respect to the bone;
    deactivating at least a portion of the virtual instrument;
    attaching the physical instrument to the bone using the grid to identify the desired position for attachment of the physical instrument to the bone.

11. The method of claim 10, further comprising:
    activating at least one virtual drill bit, after deactivating the virtual instrument, that corresponds with at least one hole of the virtual instrument when the virtual instrument is in the desired position.

12. The method of claim 11, further comprising:
    drilling at least one hole corresponding with and aligned with the virtual drill bit and inserting a drill bit or pin into the drilled hole.

13. The method of claim 12, wherein the attaching of the physical instrument includes inserting the drill bit or pin, into a corresponding hole in the physical instrument.

14. The method of claim 10, further comprising:
    drilling at least one hole corresponding to at least one hole of the virtual instrument when the virtual instrument is at the identified desired position with respect to the grid.

15. A method for generating and using a virtual instrument in a surgical procedure, comprising:
    attaching a grid to a bone;
    using a mixed or augmented reality system to produce a virtual instrument, wherein the virtual instrument is a virtual representation of a physical instrument;
    superimposing the virtual instrument over the grid;
    using the grid to identify a desired position of the virtual instrument with respect to the bone;
    attaching the physical instrument to the bone using the grid to identify the desired position for attachment of the physical instrument to the bone.

16. The method of claim 15, further comprising deactivating the virtual instrument prior to activating the physical instrument.

17. The method of claim 16, further comprising:
    activating at least one virtual drill bit, after deactivating the virtual instrument, that corresponds with at least one hole of the virtual instrument when the virtual instrument is in the desired position.

18. The method of claim 17, further comprising:
    drilling at least one hole corresponding with and aligned with the virtual drill bit and inserting a drill bit or pin into the drilled hole.

19. The method of claim 18, wherein the attaching of the physical instrument includes inserting the drill bit or pin, into a corresponding hole in the physical instrument.

20. The method of claim 15, further comprising:
    drilling at least one hole corresponding to at least one hole of the virtual instrument when the virtual instrument is at the identified desired position with respect to the grid.

21. The method of claim 15, wherein the mixed or augmented reality system includes a mixed or augmented reality headset.

22. The method of claim 15, wherein a user of the mixed or augmented reality system manipulates the position of 5 virtual instrument when superimposing the virtual instrument over the grid.

* * * * *